US012741925B2

(12) United States Patent
Sato et al.

(10) Patent No.: US 12,741,925 B2
(45) **Date of Patent: *Sep. 22, 2026**

(54) INHIBITOR FOR $RuO_4$ GAS GENERATION AND METHOD FOR INHIBITING $RuO_4$ GAS GENERATION

(71) Applicant: TOKUYAMA CORPORATION, Yamaguchi (JP)

(72) Inventors: Tomoaki Sato, Yamaguchi (JP); Yuki Kikkawa, Yamaguchi (JP); Takafumi Shimoda, Yamaguchi (JP); Takayuki Negishi, Yamaguchi (JP)

(73) Assignee: TOKUYAMA CORPORATION, Yamaguchi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/440,134

(22) Filed: Feb. 13, 2024

(65) Prior Publication Data

US 2024/0182404 A1 Jun. 6, 2024

Related U.S. Application Data

(63) Continuation of application No. 17/266,283, filed as application No. PCT/JP2020/035677 on Sep. 23, 2020, now Pat. No. 11,932,590.

(30) Foreign Application Priority Data

| | | |
|---|---|---|
| Sep. 27, 2019 | (JP) | 2019-176727 |
| Oct. 23, 2019 | (JP) | 2019-193081 |
| Nov. 22, 2019 | (JP) | 2019-211875 |
| Mar. 16, 2020 | (JP) | 2020-045869 |
| Jul. 8, 2020 | (JP) | 2020-117652 |

(51) Int. Cl.
*C07C 211/63* (2006.01)
*H10P 50/66* (2026.01)
*H10P 52/40* (2026.01)

(52) U.S. Cl.
CPC .......... *C07C 211/63* (2013.01); *H10P 50/667* (2026.01); *H10P 52/403* (2026.01)

(58) Field of Classification Search
None
See application file for complete search history.

(56) References Cited

U.S. PATENT DOCUMENTS

| | | | |
|---|---|---|---|
| 6,161,195 | A | 12/2000 | Konishi et al. |
| 8,114,343 | B1 | 2/2012 | Smith et al. |
| 10,361,092 | B1 | 7/2019 | Roberts et al. |
| 2002/0060202 | A1 | 5/2002 | Fukunaga et al. |
| 2003/0017419 | A1 | 1/2003 | Futase et al. |
| 2005/0092351 | A1 | 5/2005 | Saito et al. |
| 2009/0120458 | A1 | 5/2009 | Hao |
| 2012/0256122 | A1 | 10/2012 | Sato et al. |
| 2014/0076355 | A1 | 3/2014 | Hirabayashi et al. |
| 2016/0130500 | A1 | 5/2016 | Chen et al. |
| 2017/0222138 | A1 | 8/2017 | Park et al. |
| 2020/0354632 | A1 | 11/2020 | Sugimura et al. |

FOREIGN PATENT DOCUMENTS

| | | |
|---|---|---|
| EP | 3 181 726 | 6/2017 |
| EP | 3 726 565 | 10/2020 |
| JP | 5-314019 | 11/1993 |
| JP | 2002-161381 | 6/2002 |
| JP | 2008-42014 | 2/2008 |
| JP | 2011-503326 | 1/2011 |
| JP | 2014-62297 | 4/2014 |
| JP | 2019-002062 | 1/2019 |
| TW | 201504397 | 2/2015 |
| WO | 2011/074601 | 6/2011 |
| WO | 2016/068183 | 5/2016 |
| WO | 2019/142788 | 7/2019 |
| WO | 2019/150990 | 8/2019 |
| WO | 2019/151144 | 8/2019 |
| WO | 2019/151145 | 8/2019 |

OTHER PUBLICATIONS

Office Action issued Jun. 17, 2024 in U.S. Appl. No. 18/139,559.
International Search Report (ISR) issued Nov. 17, 2020 in International (PCT) Application PCT/JP2020/035677.
International Search Report issued Oct. 13, 2020 in International (PCT) Patent Application No. PCT/JP2020/026635, with category indication ("Y") of cited references.
Barak et al. (J. Org. Chem., 1989, 54(14), 3484. (Year: 1989).
Office Action issued Aug. 17, 2022, in U.S. Appl. No. 17/261,387.
Office Action issued Aug. 1, 2023 in Singapore Patent Application No. 11202203094Y.

*Primary Examiner* — Renee Claytor
*Assistant Examiner* — Jennifer C Sawyer
(74) *Attorney, Agent, or Firm* — WENDEROTH, LIND & PONACK, L.L.P.

(57) ABSTRACT

Provided are an inhibitor for $RuO_4$ gas generation used in a manufacturing process of a semiconductor element, that inhibits a $RuO_4$ gas generated when a semiconductor wafer containing ruthenium and a treatment liquid are brought into contact, and a method for inhibiting the $RuO_4$ gas. Specifically, provided is an inhibitor for $RuO_4$ gas generation for inhibiting a $RuO_4$ gas generated when a semiconductor wafer containing ruthenium and a treatment liquid are brought into contact in semiconductor formation steps, wherein the inhibitor includes an onium salt consisting of an onium ion and a bromine-containing ion. Also provided is a method for inhibiting $RuO_4$ gas generation by adding the inhibitor to a ruthenium treatment liquid or a ruthenium-containing liquid used in semiconductor formation steps.

11 Claims, No Drawings

INHIBITOR FOR $RuO_4$ GAS GENERATION AND METHOD FOR INHIBITING $RuO_4$ GAS GENERATION

This application is a continuation of U.S. application Ser. No. 17/266,283, filed Feb. 5, 2021, which is a national stage application of International application No. PCT/JP2020/035677, filed Sep. 23, 2020, and which claims priority to Japanese Patent Application No. 2019-176727, filed Sep. 27, 2019, Japanese Patent Application No. 2019- 193081, filed Oct. 23, 2019, Japanese Patent Application No. 2019-211875, filed Nov. 22, 2019, Japanese Patent Application No. 2020-045869, filed Mar. 16, 2020, and Japanese Patent Application No. 2020-117652, filed Jul. 8, 2020. The entire disclosures of the above- identified applications are incorporated herein by reference in their entirety.

TECHNICAL FIELD

The present invention relates to a novel inhibitor for ruthenium-containing gas ($RuO_4$ gas) generation and method for inhibiting $RuO_4$ gas generation to inhibit a $RuO_4$ gas to be generated when a semiconductor wafer containing ruthenium is brought into contact with a treatment liquid in a manufacturing process of a semiconductor element.

BACKGROUND ART

In recent years, microfabrication design has been promoted for the design rule for semiconductor elements, and thus the wiring resistance tends to increase. As a result of the increase in wiring resistance, the high-speed operation of a semiconductor element is markedly impaired, thus making it necessary to take countermeasures. In view of this, a desired wiring material is a wiring material having more solid electromigration resistance and a lower electric resistance value than conventional wiring materials.

Ruthenium has higher electromigration resistance than aluminum and copper which are conventional wiring materials, and ruthenium can decrease the electric resistance value of the wiring, thus attracting attention particularly as a wiring material for which the design rule for semiconductor elements is 10 nm or less. Not only in cases where ruthenium is used as a wiring material but also in cases where copper is used as a wiring material, ruthenium can prevent electromigration, and thus, using ruthenium as a barrier metal for copper wiring is under study.

In cases where ruthenium is selected as a wiring material in a wiring formation step of a semiconductor element, the wiring is formed by dry or wet etching in the same manner as in cases where a conventional wiring material is used. However, since it is difficult to etch ruthenium by dry etching with an etching gas, or to etch/remove ruthenium by CMP polishing, more precise etching is desired, and specifically, wet etching is attracting attention.

In cases where ruthenium is subjected to wet etching under alkaline conditions, ruthenium is dissolved, for example, in the form of $RuO_4^-$ or $RuO_4^{2-}$ in a treatment liquid. $RuO_4^-$ or $RuO_4^{2-}$ is changed to $RuO_4$ in a treatment liquid, and part of the $RuO_4$ is gasified and released into a gas phase. $RuO_4$ is strongly oxidative, and thus, not only is harmful to the human body but also is easily reduced to generate $RuO_2$ particles. In general, particles cause a decrease in the yield rate, which constitutes a serious problem in semiconductor formation steps. Against such a background, it is very important to inhibit the generation of a $RuO_4$ gas.

Patent Document 1 describes a chemical liquid with a pH of 12 or higher and an oxidation-reduction potential of 300 mV vs. SHE or higher as an etching liquid for a ruthenium film. In addition, a method for etching a ruthenium film using a solution of a halogen oxoate, such as hypochlorite, chlorite, and bromate, is presented.

Patent Document 2 proposes a method of oxidizing, dissolving, and removing ruthenium with an aqueous solution containing orthoperiodic acid having a pH of 11 or higher.

Patent Document 3 describes a CMP slurry containing a ruthenium-coordinated nitric oxide ligand (N—O ligand) that does not generate a $RuO_4$ gas in chemical mechanical polishing (CMP) of ruthenium.

CITATION LIST

Patent Document

Patent Document 1: Japanese Patent Laid-Open No. 2002-161381

Patent Document 2: International Publication No. WO2016/068183

Patent Document 3: Japanese Patent Laid-Open No. H5-314019

SUMMARY OF INVENTION

Technical Problem

However, based on the study by the present inventors, it has been found that there is room for improvement with respect to the conventional etching liquids described in the cited Document 1 to 3 because of the following.

For example, the method for etching ruthenium described in Patent Document 1 is intended to remove a ruthenium residue adhered to the back surface or bevels of a semiconductor substrate, and is capable of dissolving and removing ruthenium. However, Patent Document 1 does not mention anything about the inhibition of a $RuO_4$ gas, and in fact the method described in Patent Document 1 could not inhibit $RuO_4$ gas generation.

In addition, Patent Document 2 discloses a ruthenium removal composition containing orthoperiodic acid, which can etch an etching residue containing ruthenium. However, Patent Document 2 does not mention anything about the inhibition of a $RuO_4$ gas, and a $RuO_4$ gas generated during the etching treatment could not be inhibited.

Further, Patent Document 3 shows that it is possible to inhibit a toxic $RuO_4$ gas by using a CMP slurry containing a ruthenium-coordinated nitric oxide ligand (N—O ligand) in performing CMP. However, since the CMP slurry shown in Patent Document 3 is acidic, it is difficult to inhibit a $RuO_4$ gas by the CMP slurry composition shown in Patent Document 3 under alkaline conditions where the dissolution mechanism of ruthenium is different. In fact, when the ruthenium N—O ligand described in Patent Document 3 was added to an alkaline ruthenium etching liquid containing hypochlorous acid, then a $RuO_4$ gas was generated, therefore it was confirmed that there was no $RuO_4$ gas inhibitory effect.

Therefore, an object of the present invention is to provide an inhibitor for $RuO_4$ gas generation capable of inhibiting a $RuO_4$ gas, which may be generated when a semiconductor wafer containing ruthenium is brought into contact with a treatment liquid under alkaline conditions.

Solution to Problem

The present inventors diligently made a study to achieve the above object, in which addition of a variety of onium salts to a treatment liquid for semiconductor wafers containing ruthenium was investigated. Since it was not possible to inhibit a $RuO_4$ gas merely by using a treatment liquid for semiconductor wafers containing ruthenium, various additive ingredients were combined. As a result, it was found that the $RuO_4$ gas generation could be inhibited by adding a specific onium salt, thereby completing the present invention.

In other words, the composition of the present invention is as follows.

Aspect 1: An inhibitor for $RuO_4$ gas generation comprising an onium salt consisting of an onium ion and a bromine-containing ion.

Aspect 2: The inhibitor for $RuO_4$ gas generation according to Aspect 1, wherein the onium salt is a quaternary onium salt expressed by Formula (1), a tertiary onium salt expressed by Formula (2), an onium salt expressed by Formula (3), or an onium salt expressed by Formula (4).

(1)

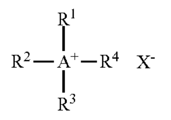

(2)

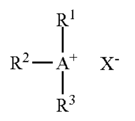

(3)

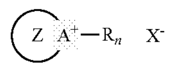

(4)

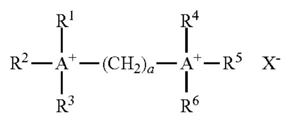

(In Formula (1), $A^+$ is an ammonium ion or a phosphonium ion; and $R^1$, $R^2$, $R^3$, and $R^4$ are independently an alkyl group with a carbon number from 1 to 25, an allyl group, an aralkyl group having an alkyl group with a carbon number from 1 to 25, or an aryl group. When $R^1$, $R^2$, $R^3$, and $R^4$ are alkyl groups, at least one of the alkyl groups in $R^1$, $R^2$, $R^3$, and $R^4$ has a carbon number of 2 or more. At least one hydrogen atom in a ring of an aryl group in the aralkyl group, or the aryl group may be replaced with a fluorine atom, a chlorine atom, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen atom may be replaced with a fluorine atom or a chlorine atom.

In Formula (2), $A^+$ is a sulfonium ion; and $R^1$, $R^2$, and $R^3$ are independently an alkyl group with a carbon number from 1 to 25, an allyl group, an aralkyl group having an alkyl group with a carbon number from 1 to 25, or an aryl group. When $R^1$, $R^2$, and $R^3$ are alkyl groups, at least one of the alkyl groups in $R^1$, $R^2$, and $R^3$ has a carbon number of 2 or more. At least one hydrogen atom in a ring of an aryl group in the aralkyl group, or the aryl group may be replaced with a fluorine atom, a chlorine atom, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen atom may be replaced with a fluorine atom or a chlorine atom.

In Formula (3), Z is an aromatic group or alicyclic group that may comprise a nitrogen atom, a sulfur atom, or an oxygen atom, and in the aromatic group or the alicyclic group, a hydrogen atom bonded to a carbon atom or a nitrogen atom may have a chlorine atom, a bromine atom, a fluorine atom, an iodine atom, at least one alkyl group with a carbon number from 1 to 15, at least one alkenyloxy group with a carbon number from 2 to 9, an aromatic group that may be substituted with at least one alkyl group with a carbon number from 1 to 15, or an alicyclic group that may be substituted with at least one alkyl group with a carbon number from 1 to 15. $A^+$ is an ammonium ion or a sulfonium ion. R is a chlorine atom, a bromine atom, a fluorine atom, an iodine atom, an alkyl group with a carbon number from 1 to 15, an allyl group, an aromatic group that may be substituted with at least one alkyl group with a carbon number from 1 to 15, or an alicyclic group that may be substituted with at least one alkyl group with a carbon number from 1 to 15. The n is an integer of 1 or 2 and indicates the number of R. When n is 2, R may be the same or different and may form a ring.

In Formula (4), $A^+$ is independently an ammonium ion, or a phosphonium ion; and $R^1$, $R^2$, $R^3$, $R^4$, $R^5$, and $R^6$ are independently an alkyl group with a carbon number from 1 to 25, an allyl group, an aralkyl group having an alkyl group with a carbon number from 1 to 25, or an aryl group. At least one hydrogen atom in a ring of an aryl group in the aralkyl group, or the aryl group may be replaced with a fluorine atom, a chlorine atom, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen atom may be replaced with a fluorine atom or a chlorine atom. The a is an integer from 1 to 10.

In Formulas (1) to (4), $X^-$ is a bromine-containing ion.)

Aspect 3: The inhibitor for $RuO_4$ gas generation according to Aspect 2, wherein the quaternary onium salt is a salt comprising at least one ammonium ion selected from the group consisting of tetraethylammonium ion, tetrapropylammonium ion, tetrabutylammonium ion, tetrapentylammonium ion, and tetrahexylammonium ion.

Aspect 4: The inhibitor for $RuO_4$ gas generation according to any one of Aspects 1 to 3, wherein the concentration of the onium salt in the inhibitor for $RuO_4$ gas generation is from 0.0001 to 50 mass %.

Aspect 5: The inhibitor for $RuO_4$ gas generation according to any one of Aspects 1 to 4, wherein the bromine-containing ion is a bromite ion, a bromate ion, a perbromate ion, a hypobromite ion, or a bromide ion.

Aspect 6: The inhibitor for $RuO_4$ gas generation according to any one of Aspects 1 to 5, wherein the concentration of hypobromite ion in the inhibitor for $RuO_4$ gas generation is 0.001 mol/L or more and 0.20 mol/L or less.

Aspect 7: The inhibitor for $RuO_4$ gas generation according to any one of Aspects 1 to 6, wherein the concentration of hypobromite ion in the inhibitor for $RuO_4$ gas generation is 0.01 mol/L or more and 0.10 mol/L or less.

Aspect 8: The inhibitor for $RuO_4$ gas generation according to any one of Aspects 1 to 7, wherein the pH of the inhibitor for $RuO_4$ gas generation at 25° C. is 8 or more and 14 or less.

Aspect 9: The inhibitor for $RuO_4$ gas generation according to any one of Aspects 1 to 8, wherein the pH of the inhibitor for $RuO_4$ gas generation at 25° C. is 12 or more and 13 or less.

Aspect 10: The inhibitor for $RuO_4$ gas generation according to any one of Aspects 1 to 9, wherein the inhibitor for $RuO_4$ gas generation comprises an oxidizing agent different from the bromine-containing ion.

Aspect 11: The inhibitor for $RuO_4$ gas generation according to Aspect 10, wherein the oxidizing agent is an oxidizing agent comprising a hypochlorite ion, or ozone.

Aspect 12 A method for inhibiting $RuO_4$ gas generation comprising a step of using the inhibitor for $RuO_4$ gas generation according to any one of Aspects 1 to 11.

Advantageous Effects of Invention

With the inhibitor for $RuO_4$ gas generation of the present invention, $RuO_4$ gas generation, which may cause particle formation or decrease in the yield rate in a semiconductor manufacturing process, can be inhibited owing to the onium salt effect. In addition, since the selectable pH range and types of oxidizing agents are expanded, it becomes possible to materialize a stable treatment liquid by selecting an appropriate oxidizing agent.

DESCRIPTION OF EMBODIMENTS (Inhibitor for $RuO_4$ Gas Generation)

An inhibitor for $RuO_4$ gas generation means a composition that inhibits $RuO_4$ gas generation when the same is added to a liquid for treating ruthenium (hereinafter referred to as "ruthenium treatment liquid"), and refers to a liquid containing an onium salt consisting of an onium ion and a bromine-containing ion.

The ruthenium treatment liquid refers to a liquid containing a component that comes into contact with ruthenium to cause physical or chemical changes to the ruthenium. Examples thereof include liquids used in steps of treating ruthenium, such as an etching step, a residue removal step, a washing step, and a CMP step, in semiconductor manufacturing processes. A liquid for cleaning ruthenium adhered to chamber inner walls, piping, etc. of each device used in the semiconductor manufacturing processes is also included.

The ruthenium treated with a ruthenium treatment liquid is wholly or partially dissolved, dispersed, or precipitated in the ruthenium treatment liquid, which becomes responsible for generation of $RuO_4$ (gas) and/or $RuO_2$ (particles). When an inhibitor for $RuO_4$ gas generation of the present invention is added to a ruthenium treatment liquid, an anion, such as $RuO_4^-$ and $RuO_4^{2-}$ (hereinafter occasionally referred to as $RuO_4^-$, etc.), present in the ruthenium treatment liquid and an onium ion form an ion pair soluble in the ruthenium solution, so as to inhibit generation of a $RuO_4$ gas and/or $RuO_2$.

(Onium Salt)

The inhibitor for $RuO_4$ gas generation of the present invention contains an onium salt to inhibit $RuO_4$ gas generation. The onium salt consists of an onium ion and a bromine-containing ion. In this regard, the bromine-containing ion is an ion that contains bromine, and examples thereof include a bromite ion, a bromate ion, a perbromate ion, a hypobromite ion, and a bromide ion.

In order for an onium salt contained in the inhibitor for $RuO_4$ gas generation of the present invention to exhibit its power of inhibiting $RuO_4$ gas generation, dissociation of the onium salt to an onium ion and a bromine-containing ion is required. This is because the onium ion generated by the dissociation of the onium salt interacts with $RuO_4^-$, etc. to inhibit $RuO_4$ gas generation. Since an onium salt comprising a halogen-containing ion easily dissociates, excellently dissolves, and can stably supply onium ions, the same can be used as an onium salt to be contained in the inhibitor for $RuO_4$ gas generation of the present invention. Among others, an onium salt comprising a bromine-containing ion is more stable and more easily synthesizable than an onium salt comprising a chlorine-containing ion, or a fluorine-containing ion, and therefore a high-purity product can be obtained industrially at a low cost. In addition, an onium salt comprising a bromine-containing ion has an advantage of containing more onium ions per unit weight than that comprising an iodine-containing ion. Therefore, an onium salt contained in the inhibitor for $RuO_4$ gas generation comprises a bromine-containing ion.

When the onium salt is contained, $RuO_4$ gas generation from the ruthenium treatment liquid can be inhibited. That is, $RuO_4^-$, etc. generated by dissolution of ruthenium are trapped in the ruthenium treatment liquid by electrostatic interaction with onium ions. Since the trapped $RuO_4^-$, etc. exist relatively stable in the treatment liquid as an ion-pair, they hardly change into $RuO_4$. As a result, the $RuO_4$ gas generation is inhibited and generation of $RuO_2$ particles is also inhibited.

As an onium salt that is effective in inhibiting a $RuO_4$ gas, those expressed by the following Formulas (1) to (4) are preferred.

(1)

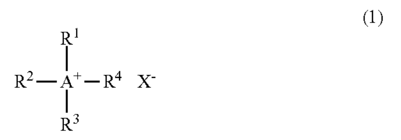

(In Formula (1), $A^+$ is an ammonium ion, or a phosphonium ion; and $R^1$, $R^2$, $R^3$, and $R^4$ are independently an alkyl group with a carbon number from 1 to 25, an allyl group, an aralkyl group having an alkyl group with a carbon number from 1 to 25, or an aryl group. When $R^1$, $R^2$, $R^3$, and $R^4$ are alkyl groups, at least one of the alkyl groups in $R^1$, $R^2$, $R^3$, and $R^4$ has a carbon number of 2 or more. At least one hydrogen atom in a ring of an aryl group in the aralkyl group, or the aryl group may be replaced with a fluorine atom, a chlorine atom, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen atom may be replaced with fluorine or chlorine. $X^-$ is a bromine-containing ion.)

(2)

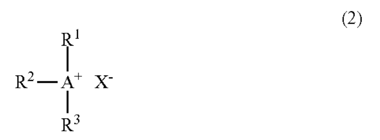

(In Formula (2), $A^+$ is a sulfonium ion; and $R^1$, $R^2$, and $R^3$ are independently an alkyl group with a carbon number from 1 to 25, an allyl group, an aralkyl group having an alkyl group with a carbon number from 1 to 25, or an aryl group. When $R^1$, $R^2$, and $R^3$ are alkyl groups, at least one of the alkyl groups in $R^1$, $R^2$, and $R^3$ has a carbon number of 2 or more. At least one hydrogen atom in a ring of an aryl group in the aralkyl group, or the aryl group may be replaced with a fluorine atom, a chlorine atom, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen atom may be replaced with a fluorine atom or a chlorine atom. $X^-$ is a bromine-containing ion.)

The alkyl groups of $R^1$, $R^2$, $R^3$, and $R^4$ in Formula (1) or (2) can be used without any particular restriction insofar as their carbon numbers are independently from 1 to 25. When the carbon number is higher, specifically when the carbon number is, for example, 3 or higher, an onium ion more strongly interacts with $RuO_4^-$, etc., so that a $RuO_4$ gas is better inhibited. On the other hand, the larger the carbon number is, the bulkier the onium ion becomes, so the ion pair to be generated at the time of the electrostatic interaction with $RuO_4^-$, etc. become less soluble in a ruthenium treatment liquid to generate precipitates. The precipitates become particles and cause decrease in the yield rate of a semiconductor element. In this regard, when the carbon number is larger, the solubility in a ruthenium treatment liquid becomes lower, and air bubbles are apt to be formed in the treatment liquid. When the solubility is higher, a larger amount of an onium salt can be dissolved in the treatment liquid, and therefore the inhibitory effect on the $RuO_4$ gas becomes higher. Conversely, when the carbon number is smaller, the interaction between the onium ions and $RuO_4^-$, etc. becomes weaker, and therefore the inhibitory effect on the $RuO_4$ gas becomes weaker. Consequently, the carbon numbers of alkyl groups in Formula (1) or (2) are independently preferably from 1 to 25, more preferably from 2 to 10, and most preferably from 3 to 6. However, when $R^1$, $R^2$, $R^3$, and $R^4$ in Formula (1) are alkyl groups, the carbon number of at least one alkyl group among $R^1$, $R^2$, $R^3$, and $R^4$ may be 2 or more; and when $R^1$, $R^2$, and $R^3$ in Formula (2) are alkyl groups, the carbon number of at least one alkyl group among $R^1$, $R^2$, and $R^3$ may be 2 or more. When an onium salt includes alkyl groups having such carbon numbers, the $RuO_4$ gas generation can be inhibited, and precipitates are less likely to be formed through interactions with $RuO_4^-$, etc. Therefore, the same can be used favorably as an inhibitor for $RuO_4$ gas generation.

The aryl groups of $R^1$, $R^2$, $R^3$, and $R^4$ in Formula (1) or (2) independently include not only an aromatic hydrocarbon, but also a heteroaryl with a heteroatom, and, although there is no particular restriction, a phenyl group and a naphthyl group are preferred. Examples of the heteroatom include nitrogen, oxygen, sulfur, phosphorus, chlorine, bromine, and iodine.

The quaternary and tertiary onium salts expressed by Formulas (1) and (2) are salts composed of an ammonium ion, a phosphonium ion, or a sulfonium ion that can exist stably in an inhibitor for $RuO_4$ gas generation, or a ruthenium treatment liquid. In general, the alkyl chain length of these ions can be easily controlled, and it is also easy to introduce an allyl group or an aryl group. This makes it possible to control the size, symmetry, hydrophilicity, hydrophobicity, stability, solubility, charge density, surface active performance, etc. of the ions, and such properties of salts composed of these ions can be similarly controlled. Such salts can be used as an onium salt represented by Formula (1) or (2) according to the present invention.

(3)

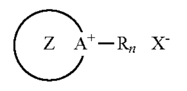

(In Formula (3), Z is an aromatic group or alicyclic group that may comprise a nitrogen atom, a sulfur atom, or an oxygen atom, and in the aromatic group or the alicyclic group, a hydrogen atom bonded to a carbon atom or a nitrogen atom may have a chlorine atom, a bromine atom, a fluorine atom, an iodine atom, at least one alkyl group with a carbon number from 1 to 15, at least one alkenyloxy group with a carbon number from 2 to 9, an aromatic group that may be substituted with at least one alkyl group with a carbon number from 1 to 15, or an alicyclic group that may be substituted with at least one alkyl group with a carbon number from 1 to 15. $A^+$ is an ammonium ion or a sulfonium ion. R is a chlorine atom, a bromine atom, a fluorine atom, an iodine atom, an alkyl group with a carbon number from 1 to 15, an allyl group, an aromatic group that may be substituted with at least one alkyl group with a carbon number from 1 to 15, or an alicyclic group that may be substituted with at least one alkyl group with a carbon number from 1 to 15. Then is an integer of 1 or 2 and indicates the number of R. When n is 2, R may be the same or different and may form a ring. $X^-$ is a bromine-containing ion.)

An onium salt having the above structure can exist stably in an alkaline inhibitor for $RuO_4$ gas generation or ruthenium treatment liquid. In this regard, the solubility of the onium salt in the inhibitor for $RuO_4$ gas generation or ruthenium treatment liquid, and the stability of ion pairs of the onium ion and $RuO_4$, etc. may be regulated by replacing a hydrogen atom bonded to a carbon or a nitrogen atom in the aromatic group or alicyclic group of Z in Formula (3) with an alkyl group, an aromatic group substituted with an alkenyloxy group, or an alicyclic group substituted with an alkyl group each having a suitable carbon number, or by appropriately selecting for R from an alkyl group, an allyl group, an aromatic group which may be substituted with an alkyl group, or an alicyclic group which may be substituted with an alkyl group.

Examples of the onium ions include cations such as imidazolium ion, pyrrolidinium ion, pyridinium ion, piperidinium ion, ammonium ion, phosphonium ion, fluoronium ion, chloronium ion, bromonium ion, iodonium ion, oxonium ion, sulfonium ion, selenonium ion, telluronium ion, arsonium ion, stibonium ion, and bismuthonium ion; and imidazolium ion, pyrrolidinium ion, pyridinium ion, piperidinium ion, and oxazolium ion are preferable.

Specific examples of onium salts comprising these onium ions include 1-butyl-2,3-dimethylimidazolium bromide, 1-hexyl-3-methylimidazolium bromide, 1-methyl-3-n-octylimidazolium bromide, 1-butyl-1-methylpyrrolidinium bromide, 1-ethyl-1-methylpyrrolidinium bromide, 1-butyl-1-methylpiperidinium bromide, 5-azoniaspiro[4,4]nonane bromide, 1-methylpyridinium bromide, 1-ethylpyridinium bromide, and 1-propylpyridinium bromide.

(4)

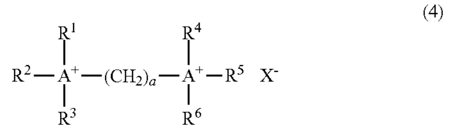

(In Formula (4), $A^+$ is independently an ammonium ion, or a phosphonium ion; and $R^1$, $R^2$, $R^3$, $R^4$, $R^5$, and $R^6$ are independently an alkyl group with a carbon number from 1 to 25, an allyl group, an aralkyl group having an alkyl group with a carbon number from 1 to 25, or an aryl group. At least one hydrogen atom in a ring of an aryl group in the aralkyl group, or the aryl group may be replaced with a fluorine atom, a chlorine atom, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen atom may be replaced with a fluorine atom or a chlorine atom. The a is an integer from 1 to 10. $X^-$ is a bromine-containing ion.)

The alkyl groups of $R^1$, $R^2$, $R^3$, $R^4$, $R^5$, and $R^6$ in Formula (4) can be used without any particular restriction insofar as their carbon numbers are independently from 1 to 25. The valence of an onium salt represented by Formula (1) above is 1, but the one represented by Formula (4) is a dication with a valence of 2, so it is apt to be bound to $RuO_4^-$, etc. by a stronger electrostatic interaction. For this reason, even when the carbon number of an alkyl group in Formula (4) is smaller than that in Formula (1), it exerts an inhibitory effect on a $RuO_4$ gas. For these reasons, the carbon numbers of the alkyl groups in Formula (4) are independently preferably from 1 to 25, more preferably from 1 to 10, and most preferably from 1 to 6. When the onium salt includes alkyl groups having such carbon numbers, the $RuO_4$ gas generation can be inhibited through interactions with $RuO_4^-$, etc., and precipitates are less likely to be formed. Therefore, the same can be used favorably as an inhibitor for $RuO_4$ gas generation.

The aryl groups of $R^1$, $R^2$, $R^3$, $R^4$, $R^5$, and $R^6$ in Formula (4) independently include not only an aromatic hydrocarbon but also a heteroaryl containing a heteroatom, and, although there are no particular restrictions, a phenyl group and a naphthyl group are preferable. Examples of the heteroatom include nitrogen, oxygen, sulfur, phosphorus, chlorine, bromine, and iodine.

The onium salt expressed by Formula (4) is composed of an ammonium ion or a phosphonium ion that can exist stably in an inhibitor for $RuO_4$ gas generation or a ruthenium treatment liquid. In general, it is easy to regulate the alkyl chain length of an ammonium ion or a phosphonium ion, and it is also easy to introduce an allyl group or an aryl group. This makes it possible to control the size, symmetry, hydrophilicity, hydrophobicity, stability, solubility, charge density, surface active performance, etc. of the ammonium ion or the phosphonium ion.

Examples of the onium salt expressed by Formula (4) which can be suitably applied may include hexamethonium bromide, and decamethonium bromide. An inhibitor for $RuO_4$ gas generation containing such an onium salt can inhibit generation of a $RuO_4$ gas and $RuO_2$ particles especially in a treatment of ruthenium.

As the quaternary onium salt expressed by Formula (1) contained in the inhibitor for $RuO_4$ gas generation of the present invention, an ammonium salt is preferable, because the stability is excellent and a high-purity industrial product thereof is easily available at a low price. Among others a tetraalkylammonium salt is preferable as the onium salt, because it is extremely stable and easily synthesizable. Specific examples thereof include salts comprising a tetraethylammonium ion, a tetrapropylammonium ion, a tetrabutylammonium ion, a tetrapentylammonium ion, and a tetrahexylammonium ion. An inhibitor containing the onium salt can inhibit especially generation of a $RuO_4$ gas and $RuO_2$ particles in a treatment of ruthenium.

The concentration of the onium salt in the inhibitor for $RuO_4$ gas generation is preferably from 0.0001 to 50 mass %. When the concentration of the onium salt is too small, not only the interaction with $RuO_4^-$, etc. is weakened to reduce the inhibitory effect on a $RuO_4$ gas is reduced, but also the amount of $RuO_4^-$, etc. soluble in a ruthenium treatment liquid is decreased to reduce the number of times of reuse of the ruthenium treatment liquid. On the other hand, when its addition amount is too large, the amount of onium ions adsorbed on the ruthenium surface increases to cause reduction in the dissolution rate of ruthenium or non-uniform etching of the ruthenium surface. Therefore, it is preferable that the inhibitor for $RuO_4$ gas generation of the present invention contains an onium salt at from 0.0001 to 50 mass %, more preferably at from 0.01 to 35 mass %, and further preferably at from 0.1 to 20 mass %. The concentration ranges of the onium salt in a liquid mixture of an inhibitor for $RuO_4$ gas generation and a ruthenium treatment liquid can be adjusted to the aforedescribed concentration ranges. When the onium salt is added, one kind can be added, or a combination of two or more kinds can be added. When two or more kinds of onium salts are added, it is possible to inhibit effectively $RuO_4$ gas generation insofar as the total concentration of onium salts is in the above concentration range. The above concentration ranges of the onium salt can be applied to any of the onium salts expressed by Formulas (1) to (4).

(Oxidizing Agent)

The inhibitor for $RuO_4$ gas generation of the present invention can contain an oxidizing agent. The oxidizing agent refers to one that has the ability to substantially dissolve ruthenium contained in a semiconductor wafer. As the oxidizing agent any of publicly known oxidizing agents that can dissolve ruthenium can be used without any particular restriction. Examples of the oxidizing agent include, but are not limited to, halogen oxyacid and permanganic acid and their salts, hydrogen peroxide, ozone, and a cerium (IV) salt. In this regard, the halogen oxyacid means hypochlorous acid, chlorous acid, chloric acid, perchloric acid, hypobromous acid, bromous acid, bromic acid, perbromic acid, hypoiodous acid, iodous acid, iodic acid, metaperiodic acid, orthoperiodic acid, periodic acid, and ions thereof. Since the oxidizing agent can dissolve ruthenium contained in a wafer, dissolution of ruthenium and inhibition of $RuO_4$ gas generation can be carried out at the same time by using the inhibitor for $RuO_4$ gas generation containing the oxidizing agent and onium salt. Further, addition of an oxidizing agent promotes dissolution of ruthenium, as well as redissolution of precipitated $RuO_2$ particles. Therefore, a ruthenium-containing wafer can be treated efficiently while inhibiting generation of a $RuO_4$ gas and $RuO_2$ particles by using the inhibitor for $RuO_4$ gas generation containing the onium salt and oxidizing agent.

Among the oxidizing agents, from the viewpoints that they can be used stably under alkaline conditions, and in a broad concentration range, halogen oxyacid, an ion of halogen oxyacid, hydrogen peroxide, or ozone is suitable as the oxidizing agent; hypochlorous acid, hypobromous acid, metaperiodic acid, orthoperiodic acid, ions thereof, or ozone is more suitable; hypochlorous acid, hypobromous acid, a hypochlorite ion, a hypobromite ion, or ozone is further suitable; a hypobromite ion, a hypochlorite ion, or ozone is still further suitable; and a hypobromite ion, or a hypochlorite ion is most preferable. These oxidizing agents can also be present in a treatment liquid as salts, which are preferably, for example, a tetraalkylammonium hypochlorite, or a tetraalkylammonium hypobromite; and more preferably tetramethylammonium hypochlorite, or tetramethylammonium hypobromite. An oxidizing agent to be contained in a treatment liquid can be composed of one kind, or two or more kinds. For example, when bromine-containing ions are contained as an oxidizing agent in the inhibitor for $RuO_4$ gas generation, the inhibitor for $RuO_4$ gas generation can further include an oxidizing agent different from the bromine-containing ions. As such an oxidizing agent different from the bromine-containing ions, an oxidizing agent containing hypochlorite ions or ozone is preferable, and an oxidizing agent containing hypochlorite ions is more preferable. The reasons therefor will be described below taking a case where the bromine-containing ion is a hypobromite ion as an example. A hypobromite ion is reduced to $Br^-$ by oxidation of ruthenium, etc., natural decomposition, decomposition by ultraviolet light, thermal decomposition, or contact with a reducing agent or an acid. Since $Br^-$ does not dissolve ruthenium, has a low inhibitory effect on a $RuO_4$ gas, and does not re-dissolve $RuO_2$ particles, the inhibitory power on $RuO_4$ gas generation tends to decline due to decrease in hypobromite ions. When the inhibitor for $RuO_4$ gas generation of the present invention contains an appropriate oxidizing agent different from hypobromite ions, such as hypochlorite ions or ozone, $Br^-$ produced by reduction or decomposition can be re-oxidized to hypobromite ions, so that the decline of the inhibitory power on $RuO_4$ gas generation due to decrease in hypobromite ions can be mitigated. In other words, when hypobromite ions and an appropriate oxidizing agent are contained in a treatment liquid, the stability of an inhibitor for $RuO_4$ gas generation is improved. As such an oxidizing agent, it is required that the oxidation-reduction potential between the oxidizing agent and a chemical species formed by reduction of the oxidizing agent exceeds the oxidation-reduction potential of the hypobromite ion/$Br^-$ system, and among others hypochlorite ions or ozone is preferable, because $Br^-$ can be efficiently oxidized to a hypobromite ion.

There is no particular restriction on a method for producing the above tetramethylammonium hypochlorite or tetramethylammonium hypobromite, and those produced by various publicly known methods can be used. For example, tetramethylammonium hypochlorite, or tetramethylammonium hypobromite produced by a method, in which chlorine or bromine is blown into tetramethylammonium hydroxide, a method, in which hypochlorous acid or hypobromous acid is mixed with tetramethylammonium hydroxide, a method, in which cations in a solution of hypochlorite or hypobromite are replaced with tetramethyl ions using an ion exchange resin, a method, in which a distillate of a solution containing hypochlorite or hypobromous acid is mixed with tetramethylammonium hydroxide, can be used favorably.

Although there is no particular restriction on the concentration of the hypobromite ions in the inhibitor for $RuO_4$ gas generation of the present invention insofar as it does not depart from the spirit and scope of the present invention, it is preferably 0.001 mol/L or more and 0.20 mol/L or less in terms of the bromine element content included in hypobromite ions, more preferably 0.005 mol/L or more and 0.20 mol/L or less, and most preferably 0.01 mol/L or more and 0.10 mol/L or less. When the concentration of hypobromite ions is too low, the $RuO_2$ particles generated by dissolution of ruthenium cannot be dissolved, and there arises a risk that the yield rate of elements may be lowered due to adhesion of $RuO_2$ to a semiconductor wafer. Meanwhile, when the concentration of hypobromite ions is too high, decomposition is accelerated by oxidation of onium ions, and there arises a risk that the gas inhibition effect is decreased. The inhibitor for $RuO_4$ gas generation, in which the concentration is controlled in the above range, is capable of treating efficiently ruthenium-containing wafers, while inhibiting generation of a $RuO_4$ gas and $RuO_2$ particles.

(pH)

The pH of the inhibitor for $RuO_4$ gas generation of the present invention at 25° C. is preferably 8 or more and 14 or less. When the pH is less than 8, dissolution of ruthenium is more likely to occur via $RuO_2$ or $Ru(OH)_3$ rather than via anions such as $RuO_4^-$, etc., the gas inhibition effect of onium salts is prone to be lowered. This $RuO_2$ constitutes a source of particles, and when the pH is less than 8, there arises a problem that the generated amount of $RuO_4$ gas increases. Meanwhile, when the pH is higher than 14, the re-dissolution of $RuO_2$ is likely to be suppressed, and generation of $RuO_2$ particles becomes problematic. Therefore, in order to fully develop the inhibitory power on $RuO_4$ gas generation, the pH of the inhibitor is preferably 8 or more and 14 or less, and more preferably 12 or more and 13 or less. In this pH range, dissolved ruthenium exists as anions, such as $RuO_4^-$ or $RuO_4^{2-}$, and therefore it can easily form ion pairs together with onium ions contained in the inhibitor, to inhibit effectively $RuO_4$ gas generation.

(Other Components)

Other additives conventionally used in a treatment liquid for semiconductors can be optionally added in the inhibitor for $RuO_4$ gas generation of the present invention to the extent that the purpose of the invention is not impaired. For example, an acid, a metal corrosion inhibitor, a water-soluble organic solvent, a fluorine compound, an oxidizing agent, a reducing agent, a complexing agent, a chelating agent, a surfactant, a defoaming agent, a pH adjuster, and a stabilizer can be added as other additives. These additives can be added singly, or in combination of two or more kinds thereof.

The inhibitor for $RuO_4$ gas generation of the present invention may contain alkali metal ions, alkaline earth metal ions, or the like derived from the aforedescribed additives, or due to circumstances during a manufacturing process of the inhibitor for $RuO_4$ gas generation. For example, sodium ions, potassium ions, or calcium ions may be contained. However, since these alkali metal ions, alkaline earth metal ions, etc. are harmful to a semiconductor element (adverse effects such as reduction of the yield rate of a semiconductor wafer, etc.), if they remain on a semiconductor wafer, their amount should preferably be small, and practically they should substantially not be contained. Therefore, for example, as the pH adjuster, an organic alkali such as ammonia, amine, choline, or tetraalkylammonium hydroxide, is preferable, rather than an alkali metal hydroxide such as sodium hydroxide, or an alkaline earth metal hydroxide.

Specifically, the total amount of alkali metal ions and alkaline earth metal ions is preferably 1 mass % or less, more preferably 0.7 mass % or less, further preferably 0.3 mass % or less, especially preferably 10 ppm or less, and most preferably 500 ppb or less.

In the inhibitor for $RuO_4$ gas generation of the present invention, the remaining component except the onium salt and other additives is water. The water contained in the inhibitor is preferably water which is made free from metal ions, organic impurities, and particles by any one of distillation, ion exchange, filtration, and various kinds of adsorption treatments, and the water is particularly preferably pure water or ultrapure water. Such water can be obtained by a known method widely utilized for semiconductor production.

(Method for Inhibiting $RuO_4$ Gas Generation)

The method for inhibiting $RuO_4$ gas generation is a method comprising a step of adding an inhibitor for $RuO_4$ gas generation of the present invention to a ruthenium treatment liquid. Specifically, the $RuO_4$ gas generation can be inhibited by adding an inhibitor for $RuO_4$ gas generation of the present invention to a ruthenium treatment liquid used in the etching step, residue removal step, washing step, CMP step, etc. in a semiconductor manufacturing process. In addition, the $RuO_4$ gas generation can be inhibited by using the inhibitor for $RuO_4$ gas generation of the present invention, when ruthenium adhered to chamber inner walls, piping, etc. of each device used in the semiconductor manufacturing process is cleaned off. For example, on the occasion of a maintenance of equipment that forms Ru using physical vapor deposition (PVD), chemical vapor deposition (CVD), atomic layer deposition (ALD), or the like, it becomes possible to inhibit $RuO_4$ gas generation during cleaning by adding the inhibitor for $RuO_4$ gas generation to a cleaning liquid used at the time of removing Ru adhered to chambers, pipes, or the like. According to this method, the $RuO_4$ gas generation can be inhibited by the mechanism described above.

For example, when the inhibitor for $RuO_4$ gas generation of the present invention is used in a ruthenium wiring formation step, the procedure is as follows. First, a substrate made of a semiconductor (e.g. Si) is prepared. The prepared substrate is subjected to an oxidation treatment to form a silicon oxide film on the substrate. Then, an interlayer insulating film constituted with a low-dielectric-constant (low-k) film is formed and via holes are formed at predetermined intervals. After the formation of the via holes, they are filled with ruthenium by thermal CVD, and a ruthenium film is further deposited thereon. The ruthenium film is etched by a ruthenium treatment liquid to which the inhibitor for $RuO_4$ gas generation has been added, and is thereby planarized while $RuO_4$ gas generation is inhibited. This makes it possible to form highly reliable ruthenium wiring in which generation of $RuO_2$ particles is inhibited. Additionally, the ruthenium treatment liquid to which the inhibitor for $RuO_4$ gas generation has been added can be used also to remove ruthenium adhered to the bevels of a semiconductor wafer.

The inhibitor for $RuO_4$ gas generation can inhibit $RuO_4$ gas generation not only in a ruthenium treatment liquid but also in a liquid after treating ruthenium (hereinafter referred to as ruthenium-containing liquid). In this regard, the ruthenium-containing liquid means a liquid that contains even a small amount of ruthenium. There is no particular restriction on the ruthenium contained in the ruthenium-containing liquid, insofar as it includes a ruthenium element without limitation to a ruthenium metal. Examples thereof include Ru, $RuO_4^-$, $RuO_4^{2-}$, $RuO_4$, $RuO_2$, and a ruthenium complex. Examples of a ruthenium-containing liquid include a waste liquid effluent from a semiconductor manufacturing process, or chamber cleaning as described above, and a treatment liquid having captured a $RuO_4$ gas in an exhaust gas treatment equipment (scrubber). When even a small amount of ruthenium is contained in a ruthenium-containing liquid, $RuO_2$ particles are formed via a $RuO_4$ gas, and they pollute a tank or piping, or accelerate deterioration of equipment due to the oxidizing effect of the particles. Further, a $RuO_4$ gas generated from ruthenium-containing liquid is strongly toxic to the human body even at a low concentration. Since a ruthenium-containing liquid has various adverse effects on the equipment and the human body as described above, it is necessary to treat it safely and rapidly while inhibiting the $RuO_4$ gas generation. When the inhibitor for $RuO_4$ gas generation of the present invention is added to a ruthenium-containing liquid, not only the $RuO_4$ gas generation can be inhibited, and the ruthenium-containing liquid is treated safely, but also the contamination or deterioration of a tank or piping of the equipment can be reduced.

When the inhibitor for $RuO_4$ gas generation of the present invention is mixed with a ruthenium treatment liquid or a ruthenium-containing liquid, the concentration of onium salts contained in the inhibitor for $RuO_4$ gas generation of the present invention is preferably so adjusted that the concentration of at least one onium salt in the liquid after mixing falls with a range from 0.0001 to 50 mass %.

The addition amount of an inhibitor for $RuO_4$ gas generation of the present invention to a ruthenium treatment liquid or a ruthenium-containing liquid can be determined considering the amount of ruthenium present in the liquid. Although there is no particular restriction on the addition amount of the inhibitor for $RuO_4$ gas generation of the present invention, it is preferably from 10 to 500,000 in terms of weight ratio with respect to the amount of the ruthenium present in a ruthenium treatment liquid or a ruthenium-containing liquid set at 1, more preferably from 100 to 100,000, and further preferably from 1000 to 50,000.

The pH at 25° C. of the liquid mixture of an inhibitor for $RuO_4$ gas generation and a ruthenium treatment liquid or a ruthenium-containing liquid is preferably for example, 7 or more and 14 or less. In order to adjust the pH of the liquid mixture, the pH adjuster illustrated above can be added.

EXAMPLES

The present invention will be described below more specifically with reference to Examples, but the present invention is not limited to these Examples.

Examples 1 to 22, Comparative Examples 1 to 4

(Preparation of Liquid Mixture of Ruthenium Treatment Liquid and Inhibitor for $RuO_4$ Gas Generation)

First, sodium hypochlorite (NaClO; produced by Wako Pure Chemical Industries, Ltd.) and ultrapure water were added in a 100 mL fluorine resin-made container, and then the pH was adjusted to the pH described in Table 1 using a 15 mass % aqueous solution of HCl, or a 1.0 mol/L aqueous solution of NaOH to yield 30 mL of a ruthenium treatment liquid. Next, an onium salt and ultrapure water were charged in a 100 mL fluorine resin-made container, and the pH was adjusted to the pH described in Table 1 similarly as described above to yield 30 mL of an inhibitor for $RuO_4$ gas generation. The onium salt in Example 21 was prepared by mixing sodium bromate and an aqueous solution of tetrapropylammonium hydroxide. The obtained ruthenium treatment liquid and inhibitor for $RuO_4$ gas generation were mixed together to yield 60 mL of a liquid mixture. Meanwhile, in Comparative Examples 1 to 4, 30 mL of ultrapure water adjusted to the same pH as the ruthenium treatment liquid was mixed in place of the inhibitor for $RuO_4$ gas generation. With respect to the ruthenium treatment liquid, to which sodium hypochlorite was added, it was confirmed that the oxidizing agent concentration was 0.56 mol/L (4.0 mass % as the effective chlorine concentration).

(Method of Measuring pH)

The pH of 10 mL of the liquid mixture prepared in each of Examples and Comparative Examples was measured using a tabletop PH meter (LAQUA F-73; manufactured by Horiba, Ltd.). The pH was measured after each liquid mixture was prepared and stabilized at 25° C.

(Quantitative Evaluation of $RuO_4$ Gas)

The generation amount of $RuO_4$ gas was measured by ICP-OES. Into an airtight container, 5 mL of the liquid mixture was placed, and one piece of Si wafer with a size of 10 mm×20 mm, on which a ruthenium film having a thickness of 1200 Å was formed, was immersed in the liquid at 25° C. or 50° C. until all ruthenium was dissolved. The temperatures of the liquid mixture (treatment temperature) during the immersion is shown in Table 1 or Table 2. Then, an air flow was passed through the airtight container, and the gas phase in the airtight container was bubbled into the absorbing liquid (1 mol/L NaOH) in a container to cause the $RuO_4$ gas generated during the immersion of the wafer to be trapped in the absorbing liquid. The amount of ruthenium in this absorbing liquid was measured by ICP-OES to determine the amount of Ru in the generated $RuO_4$ gas. The amount of Ru in the $RuO_4$ gas in Table 1 is a value obtained by dividing the weight of ruthenium contained in the absorbing liquid by the area of the immersed wafer. Whether all ruthenium on the Si wafer immersed in the liquid mixture was dissolved was verified by using a four-probe resistivity meter (Loresta-GP; manufactured by Mitsubishi Chemical Analytech Co., Ltd.) to measure the sheet resistances before and after immersion, which were converted to film thicknesses.

Example 23 and Comparative Example 5

A liquid mixture was prepared in the same manner as in Example 1 or Comparative Example 1, except that a 0.07 mol/L orthoperiodic acid ($H_5IO_6$; (produced by Fujifilm Wako Pure Chemical Corporation) was used as the oxidizing agent. Using this liquid mixture, the pH measurement and quantitative evaluation of a $RuO_4$ gas were carried out similarly as in Example 1.

Examples 24 to 28

A liquid mixture was prepared in the same manner as in Example 4, except that a 0.002, 0.02, 0.2, 0.4, or 0.6 mol/L sodium hypobromite (NaBrO; produced by Kanto Chemical Co., Ltd.) was used as the oxidizing agent. The concentration of sodium hypobromite in the liquid mixture was checked using an ultraviolet and visible spectrophotometer (UV-2600, manufactured by Shimadzu Corporation). Using this liquid mixture, the pH measurement and quantitative evaluation of a $RuO_4$ gas were carried out similarly as in Example 1.

Example 29

A liquid mixture was prepared in the same manner as in Example 4, except that an inhibitor for $RuO_4$ gas generation further comprising a 0.56 mol/L sodium hypochlorite was used. Using this liquid mixture, the pH measurement and quantitative evaluation of a $RuO_4$ gas were carried out similarly as in Example 1.

Examples 30 to 51

(Preparation of Liquid Mixture of Ruthenium-Containing Liquid and Inhibitor for $RuO_4$ Gas Generation)

Sodium hypochlorite (produced by Wako Pure Chemical Industries, Ltd.) and ultrapure water were added in a 100 mL fluorine resin-made container to yield 30 mL of a ruthenium treatment liquid. The pH of the ruthenium treatment liquid was adjusted to the same value as the pH of the ruthenium-containing liquid set forth in Table 2 using a 15 mass % aqueous solution of HCl or a 1.0 mol/L aqueous solution of NaOH. Six pieces of Si wafers with a size of 10 mm×20 mm, on which a 2400 Å thick ruthenium film was deposited were immersed in 30 mL of the obtained treatment liquid at 25° C. until the entire ruthenium was dissolved to obtain the ruthenium-containing liquid described in Table 2. The concentration of ruthenium in the ruthenium-containing liquid measured by ICP-OES is shown in Table 2.

Next, an onium salt and ultrapure water were added in a 100 mL fluorine resin-made container, and the pH was adjusted to the pH as described in Table 2 to yield 30 mL of an inhibitor for $RuO_4$ gas generation. The onium salt in Example 50 was prepared by mixing sodium bromate and an aqueous solution of tetrapropylammonium hydroxide.

With respect to the obtained liquid (liquid mixture) in which a ruthenium-containing liquid and an inhibitor for $RuO_4$ gas generation were mixed together, the pH of the liquid mixture was measured by the method described in Example 1, and then the quantitative evaluation of a $RuO_4$ gas generated from the liquid mixture was performed. The temperature of the liquid mixture during wafer immersion (processing temperature) is shown in Table 2. However, since the liquid mixture already contained ruthenium, dissolution of ruthenium was not performed in the quantitative evaluation of the $RuO_4$ gas.

Example 52

A liquid mixture was prepared in the same manner as in Example 30, except that a 0.035 mol/L orthoperiodic acid (produced by Fujifilm Wako Pure Chemical Corporation) was used as the oxidizing agent. Using this liquid mixture, the quantitative evaluation of $RuO_4$ gas was carried out similarly as in Example 30.

Examples 53 to 57

A liquid mixture was prepared in the same manner as in Example 33, except that a 0.001, 0.01, 0.1, 0.2, or 0.3 mol/L sodium hypobromite was used as the oxidizing agent. The concentration of sodium hypobromite in the liquid mixture was checked using an ultraviolet and visible spectrophotometer (UV-2600, manufactured by Shimadzu Corporation). Using this liquid mixture, the quantitative evaluation of a $RuO_4$ gas was carried out similarly as in Example 30.

Example 58

Into a 1.5 L fluorine resin-made container, 0.42 g of tetrapropylammonium perruthenate and ultrapure water were added, and the pH was adjusted to the pH described in Table 2 using a 15 mass % aqueous solution of HCl, or a 1.0 mol/L aqueous solution of NaOH to yield 1 L of a ruthenium-containing liquid.

Next, an onium salt and ultrapure water were added in a 100-mL fluorine resin-made container, and the pH was adjusted to the value described in Table 2 to yield 30 mL of an inhibitor for $RuO_4$ gas generation.

With respect to a liquid prepared by mixing 30 mL of the obtained ruthenium-containing liquid, and 30 mL of the obtained inhibitor for $RuO_4$ gas generation, the quantitative evaluation of a $RuO_4$ gas was carried out at 25° C. similarly as in Example 30.

Example 59

A liquid in which 4.8 mg of $RuO_2$ powder was dispersed in 30 mL of ultrapure water was used as the ruthenium-containing liquid. The pH of the ruthenium-containing liquid was adjusted to pH 12.0 using a 15 mass % aqueous solution of HCl, or a 1.0 mol/L aqueous solution of NaOH. Next, the onium salt described in Table 2 and ultrapure water were added into a 100-mL fluorine resin-made container, and thereafter the pH was adjusted to the pH described in Table 2 to yield 30 mL of an inhibitor for $RuO_4$ gas generation. The quantitative evaluation of a $RuO_4$ gas was performed similarly as in Example 30 using a liquid mixture obtained by mixing the obtained ruthenium-containing liquid and inhibitor for $RuO_4$ gas generation.

Example 60

To ultrapure water 1.9 mg of a Ru powder and 2.4 mg of a $RuO_2$ powder were added, and the pH was adjusted to the value set forth in Table 2 using a 15 mass % aqueous solution of HCl, or a 1.0 mol/L aqueous solution of NaOH to yield 30 mL of a ruthenium-containing liquid containing $6.0\times10^{-4}$ mol/L of Ru and $6.0\times10^{-4}$ mol/L of $RuO_2$.

Next, an onium salt and ultrapure water were added in a 100-mL fluorine resin-made container, and the pH was adjusted to the value described in Table 2 to yield 30 mL of an inhibitor for $RuO_4$ gas generation.

With respect to a liquid (liquid mixture) prepared by mixing at 25° C. 30 mL of the obtained ruthenium-containing liquid, and 30 mL of the obtained inhibitor for $RuO_4$ gas generation, the quantitative evaluation of a $RuO_4$ gas was carried out similarly as in Example 30.

Example 61

Sodium hypochlorite (produced by Wako Pure Chemical Industries, Ltd.) and ultrapure water were added in a 100 mL fluorine resin-made container, and the pH was adjusted to the value set forth in Table 2 using a 15 mass % aqueous solution of HCl, or a 1.0 mol/L aqueous solution of NaOH. By adding 1.9 mg of a Ru powder and 2.4 mg of a $RuO_2$ powder to the obtained ruthenium treatment liquid, 30 mL of a ruthenium-containing liquid containing $6.0\times10^{-4}$ mol/L of Ru and $6.0\times10^{-4}$ mol/L of $RuO_2$ was obtained.

Next, an onium salt and ultrapure water were added in a 100 mL fluorine resin-made container, and the pH was adjusted to the pH described in Table 2 to yield 30 mL of an inhibitor for $RuO_4$ gas generation. With respect to the liquid in which 30 mL of the obtained ruthenium-containing liquid and 30 mL of the obtained inhibitor for $RuO_4$ gas generation were mixed, the quantitative evaluation of a $RuO_4$ gas was carried out at 25° C. similarly as in Example 30.

Comparative Examples 6 to 10

Sodium hypochlorite (produced by Wako Pure Chemical Industries, Ltd.) or orthoperiodic acid (produced by Fujifilm Corporation Wako Pure Chemical Industries, Ltd.), and ultrapure water were added in a 100 mL fluorine resin-made container, and the pH was adjusted to the pH described in Table 2 using a 15 mass % aqueous solution of HCl or a 1.0 mol/L aqueous solution of NaOH to yield 30 mL of a ruthenium treatment liquid. Six pieces of Si wafers with a size of 10 mm×20 mm, on which a 2400 Å thick ruthenium film was deposited were immersed in 30mL of the obtained ruthenium treatment liquid at 25° C. until the entire ruthenium was dissolved to obtain the ruthenium-containing liquid described in Table 2. In the case of the ruthenium-containing liquid to which sodium hypochlorite was added, it was confirmed that the concentration thereof was 0.28 mol/L (2.0 mass % as the effective chlorine concentration). To the obtained ruthenium-containing liquid, 30 mL of ultrapure water adjusted to the same pH was mixed, and the quantitative evaluation of a $RuO_4$ gas was carried out similarly as in Example 30.

TABLE 1

| | Inhibitor for $RuO_4$ gas generation | | Ruthenium treatment liquid | | pH of liquid | Treatment temperature | Amount of Ru in $RuO_4$ gas |
|---|---|---|---|---|---|---|---|
| | Onium salt | pH | Oxidizing agent | pH | mixture | [° C.] | [μg/cm²] |
| Example 1 | Tetrapropylammonium bromide (20 mass %) | 8.0 | 0.56 mol/L NaClO aqueous solution | 8.0 | 8.0 | 25 | 1.6 |
| Example 2 | Tetrapropylammonium bromide (35 mass %) | 8.0 | 0.56 mol/L NaClO aqueous solution | 8.0 | 8.0 | 25 | 0.8 |
| Example 3 | Tetrapropylammonium bromide (50 mass %) | 8.0 | 0.56 mol/L NaClO aqueous solution | 8.0 | 8.0 | 25 | 0.2 |
| Example 4 | Tetrapropylammonium bromide (10 mass %) | 12.0 | 0.56 mol/L NaClO aqueous solution | 12.0 | 12.0 | 25 | 0.4 |
| Example 5 | Tetrapropylammonium bromide (10 mass %) | 12.5 | 0.56 mol/L NaClO aqueous solution | 12.5 | 12.5 | 25 | 0.3 |
| Example 6 | Tetrapropylammonium bromide (10 mass %) | 13.0 | 0.56 mol/L NaClO aqueous solution | 13.0 | 13.0 | 25 | 0.2 |
| Example 7 | Tetrapropylammonium bromide (10 mass %) | 14.0 | 0.56 mol/L NaClO aqueous solution | 14.0 | 14.0 | 25 | 0.1 |
| Example 8 | Didodecyldimethylammonium bromide (0.02 mass %) | 12.0 | 0.56 mol/L NaClO aqueous solution | 12.0 | 12.0 | 25 | 5.2 |
| Example 9 | Didodecyldimethylammonium bromide (0.2 mass %) | 12.0 | 0.56 mol/L NaClO aqueous solution | 12.0 | 12.0 | 25 | 0.6 |
| Example 10 | n-Octyltrimethylammonium bromide (4 mass %) | 12.0 | 0.56 mol/L NaClO aqueous solution | 12.0 | 12.0 | 25 | 0.4 |
| Example 11 | Triphenylsulfonium bromide (2 mass %) | 12.0 | 0.56 mol/L NaClO aqueous solution | 12.0 | 12.0 | 25 | 0.8 |

TABLE 1-continued

| | Inhibitor for $RuO_4$ gas generation | | Ruthenium treatment liquid | | pH of liquid | Treatment temperature | Amount of Ru in $RuO_4$ gas |
|---|---|---|---|---|---|---|---|
| | Onium salt | pH | Oxidizing agent | pH | mixture | [° C.] | [μg/cm$^2$] |
| Example 12 | Butyltriphenylphosphonium bromide (0.2 mass %) | 12.0 | 0.56 mol/L NaClO aqueous solution | 12.0 | 12.0 | 25 | 0.5 |
| Example 13 | Tetrabutylammonium bromide (8 mass %) | 12.0 | 0.56 mol/L NaClO aqueous solution | 12.0 | 12.0 | 25 | 0.6 |
| Example 14 | Tetradecyltrimethylammonium bromide (8 mass %) | 12.0 | 0.56 mol/L NaClO aqueous solution | 12.0 | 12.0 | 25 | 0.7 |
| Example 15 | Hexadecyltrimethylammonium bromide (6 mass %) | 12.0 | 0.56 mol/L NaClO aqueous solution | 12.0 | 12.0 | 25 | 0.4 |
| Example 16 | n-Decyltrimethylammonium bromide (8 mass %) | 12.0 | 0.56 mol/L NaClO aqueous solution | 12.0 | 12.0 | 25 | 0.5 |
| Example 17 | Hexyltrimethylammonium bromide (8 mass %) | 12.0 | 0.56 mol/L NaClO aqueous solution | 12.0 | 12.0 | 25 | 0.7 |
| Example 18 | Hexamethonium bromide (12 mass %) | 12.0 | 0.56 mol/L NaClO aqueous solution | 12.0 | 12.0 | 25 | 0.4 |
| Example 19 | 1-Butyl-1-methylpyrrolidinium bromide (0.6 mass %) | 12.0 | 0.56 mol/L NaClO aqueous solution | 12.0 | 12.0 | 25 | 0.9 |
| Example 20 | 5-Azoniaspiro[4.4]nonane bromide (5 mass %) | 12.0 | 0.56 mol/L NaClO aqueous solution | 12.0 | 12.0 | 25 | 0.6 |
| Example 21 | Tetrapropylammonium bromate (10 mass %) | 12.0 | 0.56 mol/L NaClO aqueous solution | 12.0 | 12.0 | 25 | 0.5 |
| Example 22 | Tetrapropylammonium bromide (20 mass %) | 12.0 | 0.56 mol/L NaClO aqueous solution | 12.0 | 12.0 | 50 | 0.7 |
| Example 23 | Tetrapropylammonium bromide (20 mass %) | 8.0 | 0.07 mol/L $H_5IO_6$ aqueous solution | 8.0 | 8.0 | 25 | 0.5 |
| Example 24 | Tetrapropylammonium bromide (10 mass %) | 12.0 | 0.002 mol/L NaBrO aqueous solution | 12.0 | 12.0 | 25 | 0.5 |
| Example 25 | Tetrapropylammonium bromide (10 mass %) | 12.0 | 0.02 mol/L NaBrO aqueous solution | 12.0 | 12.0 | 25 | 0.6 |
| Example 26 | Tetrapropylammonium bromide (10 mass %) | 12.0 | 0.2 mol/L NaBrO aqueous solution | 12.0 | 12.0 | 25 | 0.4 |
| Example 27 | Tetrapropylammonium bromide (10 mass %) | 12.0 | 0.4 mol/L NaBrO aqueous solution | 12.0 | 12.0 | 25 | 0.9 |
| Example 28 | Tetrapropylammonium bromide (10 mass %) | 12.0 | 0.6 mol/L NaBrO aqueous solution | 12.0 | 12.0 | 25 | 2.4 |
| Example 29 | Tetrapropylammonium bromide (10 mass %) | 12.0 | 0.56 mol/L NaClO aqueous solution | 12.0 | 12.0 | 25 | 0.5 |
| Comparative Example 1 | None | — | 0.56 mol/L NaClO aqueous solution | 8.0 | 8.0 | 25 | 51 |
| Comparative Example 2 | None | — | 0.56 mol/L NaClO aqueous solution | 12.0 | 12.0 | 25 | 19 |
| Comparative Example 3 | None | — | 0.56 mol/L NaClO aqueous solution | 12.5 | 12.5 | 25 | 10 |
| Comparative Example 4 | None | — | 0.56 mol/L NaClO aqueous solution | 12.0 | 12.0 | 50 | 45 |
| Comparative Example 5 | None | — | 0.07 mol/L $H_5IO_6$ aqueous solution | 8.0 | 8.0 | 25 | 50 |

TABLE 2

| | Inhibitor for $RuO_4$ gas generation | | Ruthenium-containing liquid | | | pH of liquid | Treatment temperature | Amount of Ru in $RuO_4$ gas |
|---|---|---|---|---|---|---|---|---|
| | | | | Ru compound | | | | |
| | Onium salt | pH | Oxidizing agent | [mol/l] | pH | mixture | [° C.] | [μg/cm$^2$] |
| Example 30 | Tetrapropylammonium bromide (20 mass %) | 8.0 | 0.28 mol/L NaClO aqueous solution | $1.2 \times 10^{-3}$ | 8.0 | 8.0 | 25 | 1.4 |
| Example 31 | Tetrapropylammonium bromide (35 mass %) | 8.0 | 0.28 mol/L NaClO aqueous solution | $1.2 \times 10^{-3}$ | 8.0 | 8.0 | 25 | 0.6 |
| Example 32 | Tetrapropylammonium bromide (50 mass %) | 8.0 | 0.28 mol/L NaClO aqueous solution | $1.2 \times 10^{-3}$ | 8.0 | 8.0 | 25 | 0.5 |
| Example 33 | Tetrapropylammonium bromide (10 mass %) | 12.0 | 0.28 mol/L NaClO aqueous solution | $1.2 \times 10^{-3}$ | 12.0 | 12.0 | 25 | 0.7 |
| Example 34 | Tetrapropylammonium bromide (10 mass %) | 12.5 | 0.28 mol/L NaClO aqueous solution | $1.2 \times 10^{-3}$ | 12.5 | 12.5 | 25 | 0.4 |
| Example 35 | Tetrapropylammonium bromide (10 mass %) | 13.0 | 0.28 mol/L NaClO aqueous solution | $1.2 \times 10^{-3}$ | 13.0 | 13.0 | 25 | 0.2 |
| Example 36 | Tetrapropylammonium bromide (10 mass %) | 14.0 | 0.28 mol/L NaClO aqueous solution | $1.2 \times 10^{-3}$ | 14.0 | 14.0 | 25 | 0.2 |
| Example 37 | Didodecyldimethyl-ammonium bromide (0.02 mass %) | 12.0 | 0.28 mol/L NaClO aqueous solution | $1.2 \times 10^{-3}$ | 12.0 | 12.0 | 25 | 4.8 |

TABLE 2-continued

| | Inhibitor for $RuO_4$ gas generation | | Ruthenium-containing liquid | | | pH | Treatment | Amount of Ru |
|---|---|---|---|---|---|---|---|---|
| | | | | Ru compound | | of liquid | temperature | in $RuO_4$ gas |
| | Onium salt | pH | Oxidizing agent | [mol/l] | pH | mixture | [° C.] | [μg/cm$^2$] |
| Example 38 | Didodecyldimethyl-ammonium bromide (0.2 mass %) | 12.0 | 0.28 mol/L NaClO aqueous solution | $1.2 \times 10^{-3}$ | 12.0 | 12.0 | 25 | 0.4 |
| Example 39 | n-Octyltrimethyl-ammonium bromide (4 mass %) | 12.0 | 0.28 mol/L NaClO aqueous solution | $1.2 \times 10^{-3}$ | 12.0 | 12.0 | 25 | 0.5 |
| Example 40 | Triphenylsulfonium bromide (2 mass %) | 12.0 | 0.28 mol/L NaClO aqueous solution | $1.2 \times 10^{-3}$ | 12.0 | 12.0 | 25 | 0.7 |
| Example 41 | Butyltriphenylphos-phonium bromide (0.2 mass %) | 12.0 | 0.28 mol/L NaClO aqueous solution | $1.2 \times 10^{-3}$ | 12.0 | 12.0 | 25 | 0.4 |
| Example 42 | Tetrabutylammonium bromide (8 mass %) | 12.0 | 0.28 mol/L NaClO aqueous solution | $1.2 \times 10^{-3}$ | 12.0 | 12.0 | 25 | 0.5 |
| Example 43 | Tetradecyltrimethyl-ammonium bromide (8 mass %) | 12.0 | 0.28 mol/L NaClO aqueous solution | $1.2 \times 10^{-3}$ | 12.0 | 12.0 | 25 | 0.7 |
| Example 44 | Hexadecyltrimethyl-ammonium bromide (6 mass %) | 12.0 | 0.28 mol/L NaClO aqueous solution | $1.2 \times 10^{-3}$ | 12.0 | 12.0 | 25 | 0.5 |
| Example 45 | n-Decyltrimethyl-ammonium bromide (8 mass %) | 12.0 | 0.28 mol/L NaClO aqueous solution | $1.2 \times 10^{-3}$ | 12.0 | 12.0 | 25 | 0.6 |
| Example 46 | Hexyltrimethyl-ammonium bromide (8 mass %) | 12.0 | 0.28 mol/L NaClO aqueous solution | $1.2 \times 10^{-3}$ | 12.0 | 12.0 | 25 | 0.6 |
| Example 47 | Hexamethonium bromide (12 mass %) | 12.0 | 0.28 mol/L NaClO aqueous solution | $1.2 \times 10^{-3}$ | 12.0 | 12.0 | 25 | 0.5 |
| Example 48 | 1-Butyl-1-methylpyrro-lidinium bromide (0.6 mass %) | 12.0 | 0.28 mol/L NaClO aqueous solution | $1.2 \times 10^{-3}$ | 12.0 | 12.0 | 25 | 0.6 |
| Example 49 | 5-Azoniaspiro[4.4] nonane bromide (5 mass %) | 12.0 | 0.28 mol/L NaClO aqueous solution | $1.2 \times 10^{-3}$ | 12.0 | 12.0 | 25 | 0.8 |
| Example 50 | Tetrapropylammonium bromate (10 mass %) | 12.0 | 0.28 mol/L NaClO aqueous solution | $1.2 \times 10^{-3}$ | 12.0 | 12.0 | 25 | 0.6 |
| Example 51 | Tetrapropylammonium bromide (20 mass %) | 12.0 | 0.28 mol/L NaClO aqueous solution | $1.2 \times 10^{-3}$ | 12.0 | 12.0 | 50 | 0.6 |
| Example 52 | Tetrapropylammonium bromide (20 mass %) | 8.0 | 0.035 mol/L $H_5IO_6$ aqueous solution | $1.2 \times 10^{-3}$ | 8.0 | 8.0 | 25 | 0.6 |
| Example 53 | Tetrapropylammonium bromide (10 mass %) | 12.0 | 0.001 mol/L NaBrO aqueous solution | $1.2 \times 10^{-3}$ | 12.0 | 12.0 | 25 | 0.5 |
| Example 54 | Tetrapropylammonium bromide (10 mass %) | 12.0 | 0.01 mol/L NaBrO aqueous solution | $1.2 \times 10^{-3}$ | 12.0 | 12.0 | 25 | 0.5 |
| Example 55 | Tetrapropylammonium bromide (10 mass %) | 12.0 | 0.1 mol/L NaBrO aqueous solution | $1.2 \times 10^{-3}$ | 12.0 | 12.0 | 25 | 0.5 |
| Example 56 | Tetrapropylammonium bromide (10 mass %) | 12.0 | 0.2 mol/L NaBrO aqueous solution | $1.2 \times 10^{-3}$ | 12.0 | 12.0 | 25 | 0.7 |
| Example 57 | Tetrapropylammonium bromide (10 mass %) | 12.0 | 0.3 mol/L NaBrO aqueous solution | $1.2 \times 10^{-3}$ | 12.0 | 12.0 | 25 | 2.2 |
| Example 58 | Tetrapropylammonium bromide (10 mass %) | 12.0 | — | $1.2 \times 10^{-3}$ | 12.0 | 12.0 | 25 | 0.1 |
| Example 59 | Tetrapropylammonium bromide (10 mass %) | 12.0 | — | $1.2 \times 10^{-3}$ | 12.0 | 12.0 | 25 | 0.6 |
| Example 60 | Tetrapropylammonium bromide (10 mass %) | 12.0 | — | $1.2 \times 10^{-3}$ | 12.0 | 12.0 | 25 | 0.1 |
| Example 61 | Tetrapropylammonium bromide (10 mass%) | 12.0 | 0.28 mol/L NaClO aqueous solution | $1.2 \times 10^{-3}$ | 12.0 | 12.0 | 25 | 0.6 |
| Comparative Example 6 | None | — | 0.28 mol/L NaClO aqueous solution | $1.2 \times 10^{-3}$ | 8.0 | 8.0 | 25 | 53 |
| Comparative Example 7 | None | — | 0.28 mol/L NaClO aqueous solution | $1.2 \times 10^{-3}$ | 12.0 | 12.0 | 25 | 18 |
| Comparative Example 8 | None | — | 0.28 mol/L NaClO aqueous solution | $1.2 \times 10^{-3}$ | 12.5 | 12.5 | 25 | 11 |
| Comparative Example 9 | None | — | 0.28 mol/L NaClO aqueous solution | $1.2 \times 10^{-3}$ | 12.0 | 12.0 | 50 | 46 |
| Comparative Example 10 | None | — | 0.035 mol/L $H_5IO_6$ aqueous solution | $1.2 \times 10^{-3}$ | 8.0 | 8.0 | 25 | 51 |

Comparing Example 1 with Comparative Example 1 (pH 8.0), Example 4 with Comparative Example 2 (pH 12.0), and Example 5 with Comparative Example 3 (pH 12.5) respectively, it can be known that the addition of an onium salt can inhibit $RuO_4$ gas generation at all pH levels. In Examples 1 to 3, the addition amount of the onium salt was varied, and it was confirmed that the higher addition amount of the onium salt enhances the inhibitory effect on a $RuO_4$ gas.

In Examples 8 to 21, onium salts as expressed in the above Formulas (1) to (4) and different from the kinds used in Examples 1 to 7 were used, and in all cases, an inhibitory effect on $RuO_4$ gas generation was obtained. The concentration of the onium salt in Example 4 was 10 mass %, while in Example 9 it was 0.2 mass %, indicating that in Example 9 in which the carbon number of the onium salt is larger, a comparable inhibitory effect on $RuO_4$ gas generation can be obtained with a smaller addition amount.

Comparing Comparative Example 4 with Example 22, it can be seen that the addition of an onium salt inhibits $RuO_4$ gas generation also at 50° C.

Comparing Comparative Example 2 with Examples 24 to 28, it can be seen that the addition of an onium salt inhibits $RuO_4$ gas generation, even when NaBrO is used as the oxidizing agent at from 0.002 to 0.6 mol/L.

Comparing Comparative Example 5 with Example 23, it can be seen that the addition of an onium salt inhibits $RuO_4$ gas generation, even when orthoperiodic acid is used as the oxidizing agent at 0.07 mol/L.

From the results shown in Table 2, it can be seen that generation of a ruthenium-containing gas is inhibited, when an inhibitor for $RuO_4$ gas generation containing any of the onium salts expressed by Formulas (1) to (4) is added to a ruthenium-containing liquid. This demonstrates that the inhibitor for $RuO_4$ gas generation of the present invention can be used suitably for the treatment of a ruthenium-containing liquid.

The invention claimed is:

1. A ruthenium treatment liquid comprising an onium salt consisting of an onium ion and a bromine-containing ion, and an oxidizing agent comprising a hypobromite ion, wherein the hypobromite ion concentration in the ruthenium treatment liquid is 0.001 mol/L or more and 0.20 mol/L or less, and the concentration of the onium salt in the ruthenium treatment liquid is 0.0001 to 50% by mass.

2. The ruthenium treatment liquid according to claim 1, wherein the concentration of the onium salt in the ruthenium treatment liquid is 0.01 to 50% by mass.

3. The ruthenium treatment liquid according to claim 1, wherein the onium salt is a quaternary onium salt of Formula (1), a tertiary onium salt of Formula (2), an onium salt of Formula (3), or an onium salt of Formula (4):

(1)

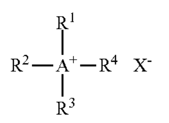

(2)

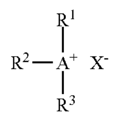

-continued (3)

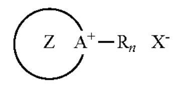

(4)

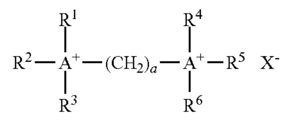

wherein in Formula (1), $A^+$ is an ammonium ion or a phosphonium ion; and $R^1$, $R^2$, $R^3$, and $R^4$ are independently an alkyl group with a carbon number from 1 to 25, an allyl group, an aralkyl group having an alkyl group with a carbon number from 1 to 25, or an aryl group; when $R^1$, $R^2$, $R^3$, and $R^4$ are alkyl groups, at least one of the alkyl groups in $R^1$, $R^2$, $R^3$, and $R^4$ has a carbon number of 2 or more; at least one hydrogen atom in a ring of an aryl group in the aralkyl group, or the aryl group may be replaced with a fluorine atom, a chlorine atom, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen atom may be replaced with a fluorine atom or a chlorine atom;

wherein in Formula (2), $A^+$ is a sulfonium ion; and $R^1$, $R^2$, and $R^3$ are independently an alkyl group with a carbon number from 1 to 25, an allyl group, an aralkyl group having an alkyl group with a carbon number from 1 to 25, or an aryl group; when $R^1$, $R^2$, and $R^3$ are alkyl groups, at least one of the alkyl groups in $R^1$, $R^2$, and $R^3$ has a carbon number of 2 or more; at least one hydrogen atom in a ring of an aryl group in the aralkyl group, or the aryl group may be replaced with a fluorine atom, a chlorine atom, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen atom may be replaced with a fluorine atom or a chlorine atom;

wherein in Formula (3), Z is an aromatic group or alicyclic group that may comprise a nitrogen atom, a sulfur atom, or an oxygen atom, and in the aromatic group or the alicyclic group, a hydrogen atom bonded to a carbon atom or a nitrogen atom may have a chlorine atom, a bromine atom, a fluorine atom, an iodine atom, at least one alkyl group with a carbon number from 1 to 15, at least one alkenyloxy group with a carbon number from 2 to 9, an aromatic group that may be substituted with at least one alkyl group with a carbon number from 1 to 15, or an alicyclic group that may be substituted with at least one alkyl group with a carbon number from 1 to 15; $A^+$is an ammonium ion or a sulfonium ion; R is a chlorine atom, a bromine atom, a fluorine atom, an iodine atom, an alkyl group with a carbon number from 1 to 15, an allyl group, an aromatic group that may be substituted with at least one alkyl group with a carbon number from 1 to 15, or an alicyclic group that may be substituted with at least one alkyl group with a carbon number from 1 to 15; the n is an integer of 1 or 2 and indicates the number of R; when n is 2, R may be the same or different and may form a ring;

wherein in Formula (4), $A^+$ is independently an ammonium ion, or a phosphonium ion; and $R^1$, $R^2$, $R^3$, $R^4$, $R^5$, and $R^6$ are independently an alkyl group with a carbon number from 1 to 25, an allyl group, an aralkyl group having an alkyl group with a carbon number from 1 to 25, or an aryl group; at least one hydrogen atom in a ring of an aryl group in the aralkyl group, or the aryl group may be replaced with a fluorine atom, a chlorine atom, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen atom may be replaced with a fluorine atom or a chlorine atom; the a is an integer from 1 to 10; and wherein in Formulas (1) to (4), $X^-$ is a bromine-containing ion.

4. The ruthenium treatment liquid according to claim 3, wherein the quaternary onium salt is a salt comprising at least one ammonium ion selected from the group consisting of tetraethylammonium ion, tetrapropylammonium ion, tetrabutylammonium ion, tetrapentylammonium ion, and tetrahexylammonium ion.

5. The ruthenium treatment liquid according to claim 1, wherein the ruthenium treatment liquid contains water.

6. The ruthenium treatment liquid according to claim 1, comprising additives, and the additives is at least one additive selected from the group consisting of a metal corrosion inhibitor, a water-soluble organic solvent, a fluorine compound, a complexing agent, a chelating agent, a surfactant, a defoaming agent, a pH adjuster, and a stabilizer.

7. The ruthenium treatment liquid according to claim 1, wherein the bromine-containing ion is a bromite ion, a bromate ion, a perbromate ion, a hypobromite ion, or a bromide ion.

8. The ruthenium treatment liquid according to claim 1, wherein the concentration of hypobromite ion in the ruthenium treatment liquid is 0.01 mol/L or more and 0.10 mol/L or less.

9. The ruthenium treatment liquid according to claim 1, wherein the pH of the ruthenium treatment liquid at 25° C. is 8 or more and 14 or less.

10. The ruthenium treatment liquid according to claim 1, wherein the ruthenium treatment liquid comprises an oxidizing agent different from the bromine-containing ion.

11. The ruthenium treatment liquid according to claim 10, wherein the oxidizing agent different from the bromine-containing ion is at least one selected from the group consisting of hypochlorite ion, ozone, orthoperiodic acid, metaperiodic acid, orthoperiodic acid ion, and metaperiodic acid ion.

* * * * *